(12) United States Patent
Taron et al.

(10) Patent No.: US 7,390,636 B2
(45) Date of Patent: Jun. 24, 2008

(54) **METHOD FOR CONSTRUCTION AND USE OF *KLUYVEROMYCES LACTIS* PROMOTER VARIANTS IN *K. LACTIS* THAT SUBSTANTIALLY LACK *E. COLI* TRANSCRIPTIONAL CAPABILITY**

(75) Inventors: Christopher Taron, Essex, MA (US); Paul Colussi, Gloucester, MA (US)

(73) Assignee: New England Biolabs, Inc., Ipswich, MA (US)

( * ) Notice: Subject to any disclaimer, the term of this patent is extended or adjusted under 35 U.S.C. 154(b) by 243 days.

(21) Appl. No.: 11/102,475

(22) Filed: Apr. 8, 2005

(65) Prior Publication Data

US 2005/0227326 A1    Oct. 13, 2005

Related U.S. Application Data

(60) Provisional application No. 60/560,418, filed on Apr. 8, 2004.

(51) Int. Cl.
*C12P 21/02*    (2006.01)
*C07H 21/04*    (2006.01)

(52) U.S. Cl. ............... 435/69.1; 435/320.1; 435/254.2; 536/24.1

(58) Field of Classification Search ............... None
See application file for complete search history.

(56) References Cited

U.S. PATENT DOCUMENTS 5,160,489 A    11/1992    Lukacsovich et al.

OTHER PUBLICATIONS

Das et al., The EMBO Journal, vol. 4, (1985), pp. 793-798.*
Colussi et al., Applied and Environmental Microbiology, vol. 71, (2005), pp. 7092-7098.*
Dickson et al., Cell 15: 123-130 (1978).
Dickson et al., Mol. Cel. Biol. 1: 1048-1056 (1981).
Dickson et al., Biotechnology 13: 19-40 (1989).
Gibbs et al., FEMS Yeast Research 4: 573-577 (2004).
Hsieh et al., Biotech. Bioeng. 67:408-416 (2000).
Wei-Guo et al., Acta Biochimica et Biophysica Sincia 28:647-52 (1996).
ISA/US, International Search Report and Written Opinion (2005).
Fleca et al. *Current Genetics* 15:261-269 (1989).
Supplemental European Search Report mailed Mar. 25, 2008, EP 05 73 4567.

* cited by examiner

*Primary Examiner*—James S Ketter
(74) *Attorney, Agent, or Firm*—Harriet M. Strimpel

(57) ABSTRACT

Methods and compositions are provided relating to production of recombinant protein in yeast. A modified $P_{LAC4}$ is described where one or more mutations may be introduced into the Pribnow box-like sequences in the promoter. The modified promoter when placed upstream of a target gene in a vector causes a significant reduction of target gene expression in transformed bacteria but produces efficient expression of the target gene in yeast.

16 Claims, 5 Drawing Sheets

SEQUENCE LISTING

<160> NUMBER OF SEQ ID NOS: 23

<210> SEQ ID NO 1
<211> LENGTH: 24
<212> TYPE: DNA
<213> ORGANISM: unknown
<220> FEATURE:
<223> OTHER INFORMATION: relevant segment of the LAC4 promoter of Kluyveromyces lactis

<400> SEQUENCE: 1
caatgtgtta tcattgtgaa gatg                              24

<210> SEQ ID NO 2
<211> LENGTH: 26
<212> TYPE: DNA
<213> ORGANISM: unknown
<220> FEATURE:
<223> OTHER INFORMATION: relevant section of LAC4 promoter of Kluyveroyces lactis

<400> SEQUENCE: 2
gagaattatt attcttttgt tatgtt                            26

```
<210> SEQ ID NO 3
<211> LENGTH: 24
<212> TYPE: DNA
<213> ORGANISM: unknown
<220> FEATURE:
<223> OTHER INFORMATION: Sequence reflecting mutated bases in LAC4
      promoter of K. lactis in vector
<220> FEATURE:
<221> NAME/KEY: mutation
<222> LOCATION: (8)..(9)
<220> FEATURE:
<221> NAME/KEY: mutation
<222> LOCATION: (11)..(11)
<220> FEATURE:
<221> NAME/KEY: mutation
<222> LOCATION: (14)..(15)
<220> FEATURE:
<221> NAME/KEY: mutation
<222> LOCATION: (17)..(17)

<400> SEQUENCE: 3
caatgtgaga acagagagaa gatg                                             24

<210> SEQ ID NO 4
<211> LENGTH: 26
<212> TYPE: DNA
<213> ORGANISM: unknown
<220> FEATURE:
<223> OTHER INFORMATION: sequence reflecting mutated bases in LAC4
      promoter of K. lactis in vector
<220> FEATURE:
<221> NAME/KEY: mutation
<222> LOCATION: (7)..(7)
<220> FEATURE:
<221> NAME/KEY: mutation
<222> LOCATION: (9)..(12)

<400> SEQUENCE: 4
gagaatgaga gctcttttgt tatgtt                                           26

<210> SEQ ID NO 5
<211> LENGTH: 25
<212> TYPE: DNA
<213> ORGANISM: unknown
<220> FEATURE:
<223> OTHER INFORMATION: primer

<400> SEQUENCE: 5
ctgttactct ctctctttca aacag                                            25

<210> SEQ ID NO 6
<211> LENGTH: 21
<212> TYPE: DNA
<213> ORGANISM: unknown
<220> FEATURE:
<223> OTHER INFORMATION: primer

<400> SEQUENCE: 6
gcatgtatac atcagtatct c                                                21

<210> SEQ ID NO 7
<211> LENGTH: 55
<212> TYPE: DNA
<213> ORGANISM: unknown
<220> FEATURE:
<223> OTHER INFORMATION: primer

<400> SEQUENCE: 7
ggtatttaat agctcgaatc aatgtgagaa cagagaagat gttcttccct aactc           55
```

<210> SEQ ID NO 8
<211> LENGTH: 70
<212> TYPE: DNA
<213> ORGANISM: unknown
<220> FEATURE:
<223> OTHER INFORMATION: primer

<400> SEQUENCE: 8
gtaatgtttt cattgctgtt ttacttgaga tttcgattga gaaaaaggta tttaatagct    60
cgaatcaatg                                                          70

<210> SEQ ID NO 9
<211> LENGTH: 37
<212> TYPE: DNA
<213> ORGANISM: unknown
<220> FEATURE:
<223> OTHER INFORMATION: primer

<400> SEQUENCE: 9
gtttcttagg agaatgagag ctcttttgtt atgttgc                             37

<210> SEQ ID NO 10
<211> LENGTH: 37
<212> TYPE: DNA
<213> ORGANISM: unknown
<220> FEATURE:
<223> OTHER INFORMATION: primer

<400> SEQUENCE: 10
gcaacataac aaaagagctc tcattctcct aagaaac                             37

<210> SEQ ID NO 11
<211> LENGTH: 30
<212> TYPE: DNA
<213> ORGANISM: unknown
<220> FEATURE:
<223> OTHER INFORMATION: primer

<400> SEQUENCE: 11
ggaagatcta tgagtaaagg agaagaactt                                     30

<210> SEQ ID NO 12
<211> LENGTH: 40
<212> TYPE: DNA
<213> ORGANISM: unknown
<220> FEATURE:
<223> OTHER INFORMATION: primer

<400> SEQUENCE: 12
ataagaatgc ggccgcttat ttgtagagct catccatgcc                          40

<210> SEQ ID NO 13
<211> LENGTH: 39
<212> TYPE: DNA
<213> ORGANISM: unknown
<220> FEATURE:
<223> OTHER INFORMATION: primer

<400> SEQUENCE: 13
ccgctcgaga aaagagatgc acacaagagt gaggttgct                           39

<210> SEQ ID NO 14
<211> LENGTH: 34
<212> TYPE: DNA
<213> ORGANISM: unknown

-continued

```
<220> FEATURE:
<223> OTHER INFORMATION: primer

<400> SEQUENCE: 14
ataagaatgc ggccgcttat aagcctaagg cagc                                34

<210> SEQ ID NO 15
<211> LENGTH: 39
<212> TYPE: DNA
<213> ORGANISM: unknown
<220> FEATURE:
<223> OTHER INFORMATION: primer

<400> SEQUENCE: 15
ccgctcgaga aaagaattgt tggtggttct gattctaga                           39

<210> SEQ ID NO 16
<211> LENGTH: 32
<212> TYPE: DNA
<213> ORGANISM: unknown
<220> FEATURE:
<223> OTHER INFORMATION: primer

<400> SEQUENCE: 16
ggaagatctc taatgtagaa aactttgtat cc                                  32

<210> SEQ ID NO 17
<211> LENGTH: 46
<212> TYPE: DNA
<213> ORGANISM: unknown
<220> FEATURE:
<223> OTHER INFORMATION: primer

<400> SEQUENCE: 17
tccgagctca agcttgaaaa aaatgaaatt ctctactata ttagcc                   46

<210> SEQ ID NO 18
<211> LENGTH: 30
<212> TYPE: DNA
<213> ORGANISM: unknown
<220> FEATURE:
<223> OTHER INFORMATION: primer

<400> SEQUENCE: 18
ccgctcgaga tcatccttgt cagcgaaagc                                     30

<210> SEQ ID NO 19
<211> LENGTH: 77
<212> TYPE: DNA
<213> ORGANISM: unknown
<220> FEATURE:
<223> OTHER INFORMATION: primer

<400> SEQUENCE: 19
cggggatcct ttcagaggcc gaactgaaga tcacagaggc ttccgctgcg gatcttgtgt    60
ccaagctggc ggccgga                                                   77

<210> SEQ ID NO 20
<211> LENGTH: 36
<212> TYPE: DNA
<213> ORGANISM: unknown
<220> FEATURE:
<223> OTHER INFORMATION: primer

<400> SEQUENCE: 20
```

```
tcccccgggc tatggagtca ccacatttcc cagcaa                                      36

<210> SEQ ID NO 21
<211> LENGTH: 36
<212> TYPE: DNA
<213> ORGANISM: unknown
<220> FEATURE:
<223> OTHER INFORMATION: primer

<400> SEQUENCE: 21
cgcggatccg ccaccatgcc tcaatcctgg gaagaa                                      36

<210> SEQ ID NO 22
<211> LENGTH: 10
<212> TYPE: DNA
<213> ORGANISM: unknown
<220> FEATURE:
<223> OTHER INFORMATION: relevant section of LAC4 promoter of K. lactis

<400> SEQUENCE: 22
ttatcattgt                                                                   10

<210> SEQ ID NO 23
<211> LENGTH: 10
<212> TYPE: DNA
<213> ORGANISM: unknown
<220> FEATURE:
<223> OTHER INFORMATION: modified section of LAC4 promoter of K. lactis

<400> SEQUENCE: 23
agaacagaga                                                                   10
```

METHOD FOR CONSTRUCTION AND USE OF *KLUYVEROMYCES LACTIS* PROMOTER VARIANTS IN *K. LACTIS* THAT SUBSTANTIALLY LACK *E. COLI* TRANSCRIPTIONAL CAPABILITY

CROSS REFERENCE

This application gains priority from U.S. Provisional Application Ser. No. 60/560,418 filed Apr. 8, 2004, herein incorporated by reference.

BACKGROUND

For over a decade, the budding yeast *Kluyveromyces lactis* (*K. lactis*) has been widely used for industrial-scale production of recombinant proteins in the food and dairy industries for reasons that include the following factors: (i) many strains of *K. lactis* grow rapidly and to extremely high cell densities in culture; (ii) *K. lactis* efficiently directs proteins to be secreted into the medium; and (iii) *K. lactis* has GRAS (Generally Regarded As Safe) FDA status which permits its use for food, agricultural and health-related applications.

A typical *K. lactis* heterologous protein production strategy involves directing a desired protein to be secreted from the cell into the growth medium. This methodology has a number of advantages over cellular expression methods: (i) the protein is produced significantly pure since *K. lactis* secretes relatively few endogenous proteins; (ii) post-translational protein modifications found only on secreted eukaryotic proteins are obtainable; and (iii) strategies to harvest protein from the medium of continuously growing cells can be devised.

A strong yeast promoter suitable for directing high levels of transcription in *K. lactis* is the *K. lactis* LAC4 promoter ($P_{LAC4}$) (Dickson, et al. *Cell* 15:123-130 (1978); Dickson, R. C., and M. I. Riley, *Biotechnology* 13:19-40 (1989); Dickson, et al. *Mol. Cel. Biol.* 1:1048-1056 (1981)). This promoter naturally drives expression of the LAC4 gene which encodes a highly expressed lactase (β-galactosidase). Transcription of LAC4 is elevated in response to the presence of lactose or galactose in growth medium where lactase allows the cell to convert lactose to fermentable sugars. Expression of heterologous proteins from $P_{LAC4}$ may achieve levels greater than 100 mg $L^{-1}$ of secreted recombinant protein in yeast fermentations.

Unfortunately, in addition to its ability to function as a strong promoter in *K. lactis*, $P_{LAC4}$ constitutively promotes gene expression in *E. coli* cells. This can be particularly problematic when trying to assemble DNA constructs harboring genes that encode a protein toxic to *E. coli* prior to their introduction into yeast cells. One approach to solving this problem has been reported by Gibbs et al. (*FEMS Yeast Research* 4: 573-577 (2004)) who utilized yeast introns in the shuttle vector. Unfortunately, this modification abolishes some but not all functional expression of potentially toxic recombinant proteins.

SUMMARY

In an embodiment of the invention, a method is provided for producing a recombinant protein in yeast cells that includes the steps of: obtaining a vector into which a gene encoding the target protein has been inserted together with a modified $P_{LAC4}$ wherein the modification results in a significant reduction in gene expression in bacteria exemplified by *E. coli*; transforming yeast cells exemplified by *K. lactis* with the vector; and producing an effective amount of recombinant protein in the yeast cells. In certain embodiments, at least 50%, more particularly at least 70%, more particularly at least 90%, of the transformed yeast cells express recombinant protein. In an embodiment of the invention, the effective amount of recombinant protein produced in yeast is substantially similar to the amount of protein from a recombinant gene under control of an unmodified $P_{LAC4}$ promoter.

The modified $P_{LAC4}$ in the method may optionally include a mutation in one or more Pribnow box-like sequences, for example in PBI, PBII and PBIII, more particularly in a first region of the promoter corresponding to nucleotides –198 to –212 or in a second region of the promoter corresponding to nucleotides –133 to –146. In certain embodiments, the modified $P_{LAC4}$ contains one or more mutations in both the first region and also one or more mutations in the second region of the promoter. In a further embodiment of the invention, nucleotides –1 to –283 in the modified $P_{LAC4}$ are substituted by nucleotides –1 to –283 of the phosphoglycerate kinase promoter from *S. cerevisiae* (PGK1).

The vector may be an episomal or an integrative plasmid in the transformed yeast cells. The vector contains a modified $P_{LAC4}$ promoter and optionally a $P_{LAC4}$ terminator. Moreover, the vector may include a DNA sequence encoding at least one of a yeast secretion signal peptide such as *K. lactis* α-mating factor (Kl α-MF), a selectable marker such as *Aspergillus nidulans* acetamidase (amdS) selectable marker gene, or a multiple cloning site for insertion of a gene encoding a recombinant protein.

The cells transformed with the above-described vector may include a host yeast cell and/or a host bacterial cell.

In an embodiment of the invention, a kit that includes a vector as described above and optionally includes competent yeast cells together with instructions for use is provided.

An embodiment of the invention provides a modified $P_{LAC4}$ Pribnow box wherein TTATCATTGT (SEQ ID NO:22) is modified to AGAACAGAGA (SEQ ID NO:23) and/or TATTATTCT is modified to GAGAGCTCT.

Genes are cloned into the multiple cloning site (MCS) in the same translational reading frame as the *S. cerevisiae* α-mating factor secretion leader sequence (Sc α-MF). Transcription is initiated and terminated by $P_{LAC4}$ and LAC4 transcription terminator sequence ($TT_{LAC4}$), respectively. The *S. cerevisiae* ADH1 promoter ($P_{ADH1}$) drives expression of a bacterial gene conferring resistance to G418 in yeast. *E. coli* vector sequence has been inserted into a unique SacII site in $P_{LAC4}$ to allow for propagation in *E. Coli*. The vector is linearized by digestion with SacII OR BstXI for integration into the LAC4 promoter locus in the *K. lactis* chromosome.

Figure 2:
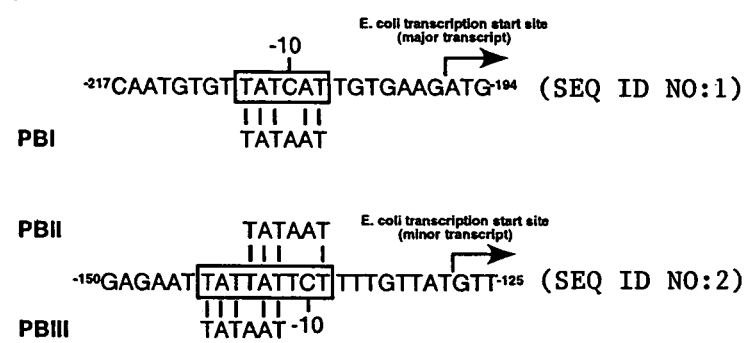
Figure 2:
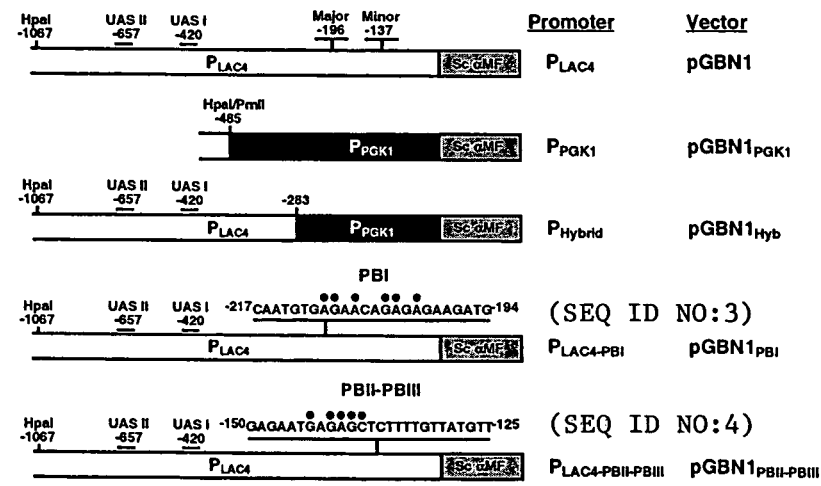

FIG. 2 shows the Pribnow box-like sequences in $P_{LAC4}$ and construction of $P_{LAC4}$ variant expression vectors.

FIG. 2A shows Pribnow box-like sequences PBI, and PBII and PBIII (SEQ ID NOS:1 and 2) relative to the major and minor *E. coli* transcription start sites associated with $P_{LAC4}$, and are aligned with the Pribnow box consensus sequence TATAAT. Nucleotides that agree with the consensus sequence are boxed.

FIG. 2B shows expression vectors containing $P_{LAC4}$ variants. The approximate positions of the *E. coli* major and minor transcription start sites are shown in the schematic for pGBN1. The approximate positions of the galactose-responsive elements, upstream activator sequence (UAS) UASI and II, are shown for each construct. Regions of $P_{LAC4}$ DNA that have been replaced with fragments of the PGK1 promoter are shown in black. Mutated bases in the Pribnow box-like sequences in the $P_{LAC4}$ DNA of plasmids pGBN1$_{PBI}$ and pGBN1$_{PBII-PBIII}$ are indicated with a black dot above each base (SEQ ID NOS:3 and 4). All numbered positions are relative to the adenine of the ATG start codon of the Sc α-MF secretion leader that has been designated position +1.

Figure 3:
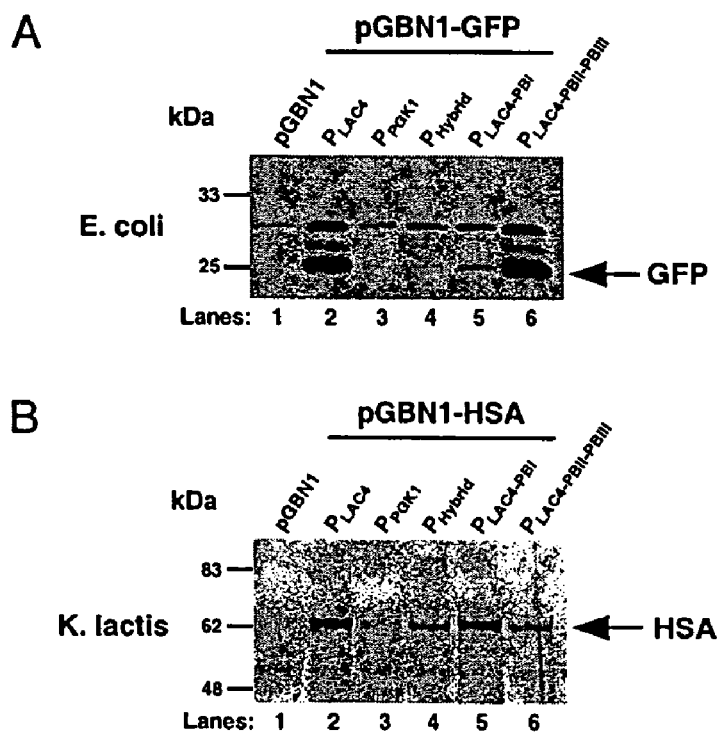

FIG. 3 shows $P_{LAC4}$ variant expression of green fluorescent protein (GFP) in *E. coli* and human serum albumin (HSA) in *K. lactis*.

FIG. 3A shows GFP cloned downstream of each of the various $P_{LAC4}$ variants. Proteins from lysates of *E. coli* carrying each expression construct were separated by SDS-PAGE, and GFP was detected by Western analysis.

Lane 1: pGBN1 used as a negative control. Lysate is derived from bacteria containing an empty pGBN1 plasmid;

Lane 2: PGBN1/$P_{LAC4}$ used as a second control containing an unmodified $P_{LAC4}$;

Lanes 3-6: lysates used from *E. coli* transformed with pGBN1 in which $P_{LAC4}$ has been substituted with $P_{PGK1}$, $P_{Hybrid}$, $P_{LAC4-PBI}$ and $P_{LAC4-PBII-PBIII}$.

FIG. 3B shows HSA cloned downstream of each $P_{LAC4}$ for expression in *K. lactis* cells. Secreted proteins in spent culture medium of *K. lactis* strains containing the various integrated HSA expression vectors were resolved by SDS-PAGE (4-20% acrylamide) and Coomassie stained. HSA ran as a single band with an apparent mass of 66 kDa.

Lane 1: spent culture medium from a yeast strain containing empty pGBN1 integrated into the chromosome as a negative control;

Lanes 2-6: spent media from *K. lactis* transformed with pGBNI$_{LAC4}$-HSA, pGBNI$_{PGK1}$- HSA, pGBNI$_{Hybrid}$-HSA, pGBNI$_{LAC4-PBI}$-HSA and pGBNI$_{LAC4-PBII-PBIII}$-HSA.

Figure 4:
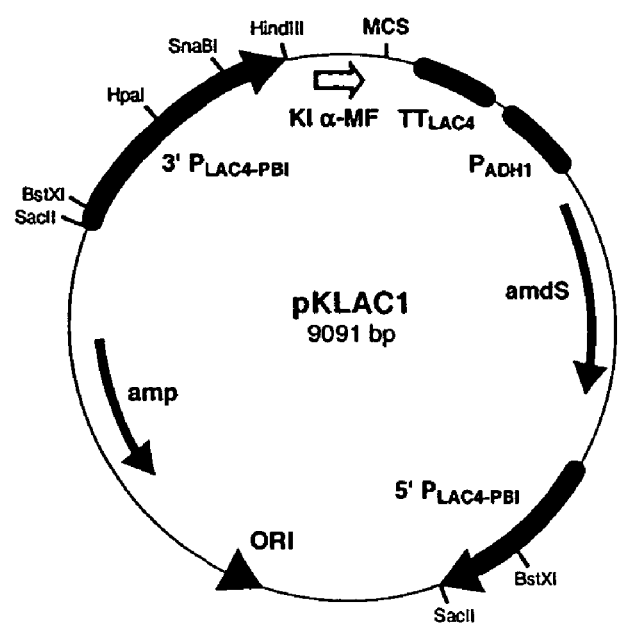

FIG. 4 shows pKLAC1, an *E. coil/K. lactis* integrative expression vector. The pKLAC1 vector (GenBank No. AY968582) is organized similarly to pGBN1 with the following modifications: (i) genes are cloned into the multiple cloning site in the same translational reading frame as the native Kl α-MF leader sequence; and (ii) expression in *K. lactis* is initiated by the $P_{LAC4-PBI}$ variant. The $P_{ADH1}$ drives expression of an acetamidase-selectable marker (amdS) gene for selection of transformants by growth on acetamide medium.

Figure 5:
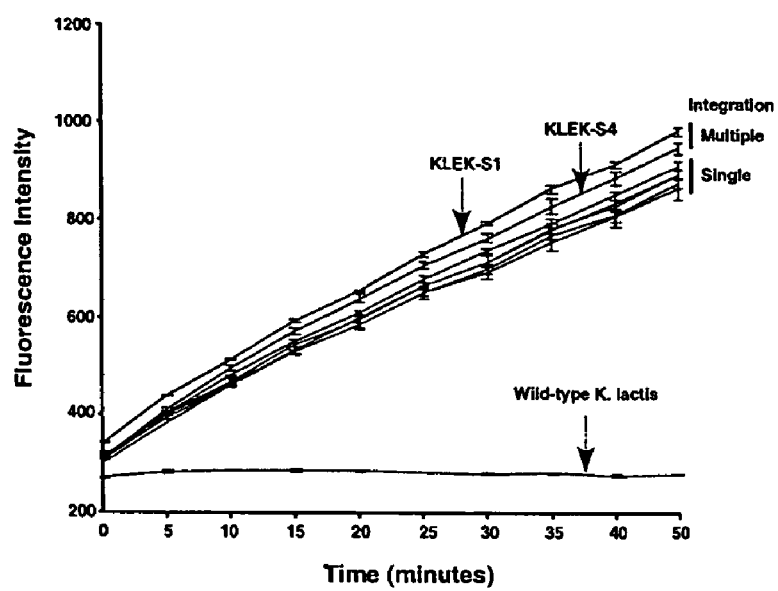

FIG. 5 shows the activity of secreted enterokinase in the spent culture medium of *K. lactis* cells containing integrated pKLAC1-EK$_L$ (the gene encoding the enterokinase catalytic subunit). Seven *K. lactis* strains harboring pKLAC1-EK$_L$ and wild-type GG799 cells were grown in YPGal medium for 48 hours. Cleared spent culture medium was assayed for enterokinase activity by measuring cleavage of a fluorogenic peptide over time. KLEK-S1 and KLEK-S4 are two strains that contain multiple copies of integrated pKLAC1-EK$_L$ as determined by Southern analysis. All other strains contain a single integrated copy of pKLAC1-EK$_L$.

DETAILED DESCRIPTION

A functional shuttle vector allows for the propagation of cloned genes in bacteria prior to their introduction into yeast cells for expression. However, yeast expression systems that utilize the strong $P_{LAC4}$ can be adversely affected by the serendipitous expression of protein from genes under control of $P_{LAC4}$ in bacterial host cells such as *E. coli*. This promoter activity can interfere with the cloning efficiency of genes whose translational products are potentially detrimental to bacteria.

Two nucleotide sequences in the $P_{LAC4}$ closely resemble the bacterial Pribnow box transcription element consensus sequence, which is TATAAT. These sequences are located approximately 10 nucleotides upstream from the site where transcription begins and are adjacent and upstream of the major and a minor transcription start sites in *E. coil* (Dickson et al. *Biotechnology* 13:19-40 (1989)). In particular, the sequences are located at –204 to –209 for the major transcript, and –144 to –136 for the minor transcript) (see boxed sequences in FIG. 2A).

The initiation sites of two RNA transcripts associated with *E. coli* expression of *K. lactis* $P_{LAC4}$ have been previously mapped to –196 bp (initiation of the major *E. coli* transcript) and –127 bp (initiation of the minor *E. coli* transcript) relative to the adenine nucleotide in the ATG start codon of the native LAC4 gene (Dickson et al. 1989).

$P_{LAC4}$ variants with mutated Pribnow box-like sequences can be created by site-directed mutagenesis which substantially retain their ability to function as strong promoters in *K. lactis* to the extent similar to that of unmutated Pribnow box-like sequences. $P_{Lac4}$ variants that have mutated Pribnow box-like sequences may retain strong promoter activity in other yeast strains from the *Kluyeromyces* species as well as *Saccharomyces* species, *Pichia* species, *Hansenula* species, *Yarrowia* species, *Neurospora* species, *Aspergillus* species, *Penicillium* species, *Candida* species, *Schizosaccharomyces* species, *Cryptococcus* species, *Coprinus* species, *Ustilago* species, *Magnaporth* species and *Trichoderma* species. Based on the knowledge in the art that DNA sequence is determinative for promoter strength, it is expected that some mutants will produce greater amounts of protein than under similar conditions using the wild-type $P_{LAC4}$. Mutation is here intended to include any of: a substitution, a deletion or an addition of one or more nucleotides in a DNA sequence.

In an embodiment of the invention, the fungal expression host is the yeast *K. lactis* and the bacterial host is *E. coli* and a series of $P_{LAC4}$ variants have been created by targeted mutagenesis of three DNA sequences (PBI, PBII and PBIII) that resemble the *E. Coli* Pribnow box element of bacterial promoters and that reside immediately upstream of two *E. coli* transcription initiation sites associated with $P_{LAC4}$. In the examples, the mutation in $P_{LAC4}$ is in the region of (a) the –198 to –212 region of the promoter (FIG. 2B) for example at positions –201, –203, –204, –207, –209 and –210. These mutations do not substantially interfere with the ability of the promoter to function as a strong promoter in *K. lactis*; (b) the –133 to –146 region of the promoter for example at positions –139, –140, –141, –142 and –144 which do not substantially interfere with strong promoter activity; or (c) the –198 to –212 and –133 to –146 regions. In a further embodiment, a hybrid promoter was created that consists of 283 bp (–1 to –283) of the *S. cerevisiae* (Sc) PGKI promoter replacing the –1 to –283 region of *K. lactis* $P_{LAC4}$ (FIG. 2B).

Overexpression of proteins in *K. lactis* and more generally in yeast involves construction of a shuttle vector containing a DNA fragment with sequences suitable for directing high-level transcription of a gene of interest upon introduction into the yeast host. The vector should contain at least one or more of the following: (i) a strong yeast promoter; (ii) DNA encoding a secretion leader sequence (if secretion of the protein into the medium is desired); (iii) the gene encoding the protein to be expressed; (iv) a transcription terminator sequence; and (v) a yeast-selectable marker gene. These sequence components are typically assembled in a plasmid vector in *E. coli* then transferred to yeast cells to achieve protein production.

$P_{LAC4}$ can function as a strong promoter for protein expression in yeast when present on an integrative plasmid or an episomal plasmid such as pKD1-based vectors, 2 micron-containing vectors, and centromeric vectors. The secretion leader sequence (if secretion of the protein into the medium is desired) may include a Sc α-MF pre-pro secretion leader peptide which has been cloned as a HindIII/XhoI fragment. Other prokaryotic or eukaryotic secretion signal peptides (e.g. *K. lactis* α-mating factor pre-pro secretion signal peptide, *K. lactis* killer toxin signal peptide) or synthetic secretion signal peptides can also be used. Alternatively, a secretion leader can be omitted from the vector altogether to achieve cellular expression of the desired protein.

An example of a transcription terminator sequence is $TT_{LAC4}$.

The yeast-selectable marker gene can be for example, G418 or an amdS gene. Expression of acetamidase in transformed yeast cells allows for their growth on medium lacking a simple nitrogen source but containing acetamide. Acetamidase breaks down acetamide to ammonia which can be utilized by cells as a source of nitrogen. A benefit of this selection method is that it enriches transformant populations for cells that have incorporated multiple tandem integrations of a pKLAC1-based expression vector and that produce more recombinant protein than single integrations (FIG. 5).

The above-described mutants $P_{LAC4}$ have been integrated into an *E. coli/K. lactis* integrative shuttle vector, for example, pGBN1 and pKLAC1 shown in FIGS. 1 and 4, respectively, which integrates into the *K. lactis* genome after transformation of competent host cells and subsequently directs protein expression.

In embodiments of the invention, at least 50%, more specifically at least 70%, preferably at least 90%, of transformants that form on acetamide plates following transformation of *K. lactis* with pKLAC1-based constructs express foreign protein, for example, HSA or the *E. coli* maltose-binding protein (MBP), toxic protease enterokinase, mouse transthyretin, toxic glue proteins from marine organisms and a bacterial cellulase. These examples are not intended to be limiting. The system has utility for any protein-encoding gene placed downstream of the mutated $P_{LAC4}$.

Levels of protein expression under $P_{LAC4}$ and mutants thereof were determined for several different proteins. For example, mutation of PBI reduced bacterial expression of a reporter protein (GFP) by ~87%, whereas mutation of PBII and PBIII had little effect on GFP expression in the bacterial host cell. Deletion of all three sequences completely eliminated GFP expression in the bacterial host cells. For HSA, the Example and FIG. 3b show that about 50 mg L$^{-1}$ of HSA was secreted by *K. lactis* when expressed from either wild-type or mutant $P_{LAC4}$.

EXAMPLE

Yeast Strains, Transformation and Culturing Conditions

The prototrophic *K. lactis* strain GG799 (MAT α [pGK11+]) was routinely grown and maintained on YPD media (1% yeast extract, 2% peptone, 2% glucose) at 30° C. Prior to transformation of GG799 cells, 1 μg of pGBN1- or pKLAC1-based expression vector containing a gene of interest was linearized by SacII digestion. Linearized expression vectors were used for integrative transformation of commercially available competent *K. lactis* GG799 cells (New England Biolabs, Beverly, Mass.) as directed by the supplier. Colonies of cells transformed with pGBN1, pGBN1$_{PGK1}$, pGBN1$_{Hyb}$, pGBN1$_{PBI}$ or pGBN1$_{PBII-PBIII}$ vectors were selected by growth on YPD agar plates containing 200 μg G418 ml$^{-1}$ (Sigma, St. Louis, Mo.) for 2-3 days at 30° C. Colonies of cells transformed with pKLAC1-based vectors were selected by growth on agar plates containing 1.17% yeast carbon base (New England Biolabs, Beverly, Mass.), 5 mM acetamide (New England Biolabs, Beverly, Mass.) and 30 mM sodium phosphate buffer pH 7 for 4-5 days at 30° C. *K. lactis* strains expressing heterologous genes were cultured in YP media containing 2% galactose (YPGal) at 30° C. for 48-96 hours.

Polymerase Chain Reaction

Primers used in this study are listed in Table 1. Amplification by PCR was performed using high fidelity Deep Vent™ DNA polymerase (New England Biolabs, Beverly, Mass.). Typical PCR mixtures contained 0.2 mM dNTPs, 0.5 μg of each primer, 1× Thermopol buffer (New England Biolabs, Mass.) and 100 ng template DNA in a total reaction volume of 100 μl. Thermocycling typically consisted of a "hot start" at 95° C. for 5 minutes followed by 30 cycles of successive incubations at 94° C. for 30 sec, 58° C. for 30 sec and 72° C. (1 min per kb of DNA). After thermocycling, a final extension was performed at 72° C. for 10 minutes.

Construction of *K. lactis* $P_{LAC4}$ Variants in pGBN1

Figure 1:
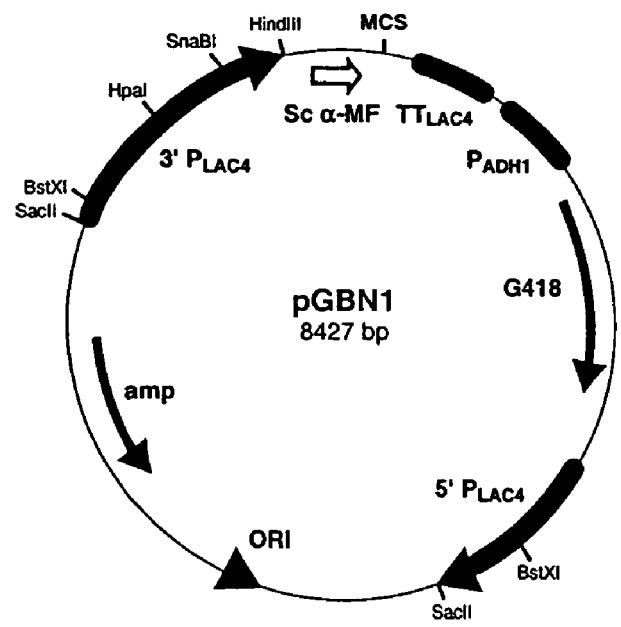
FIG. 1 shows the *E. coli/K. lactis* integrative expression vector pGBN1.

All promoter variants were derived from wild-type $P_{LAC4}$ present in the integrative expression vector pGBN1, a *K. lactis/E. coli* shuttle vector that contains 2317 bp of $P_{LAC4}$ DNA split into 1663 and 654 bp fragments that are separated by pUC19 plasmid DNA (FIG. 1). The split occurs at a unique restriction site recognized by SacII. A 2830 bp of pUC19 vector DNA sequence has been inserted at this unique restriction site. This allows the expression vector to integrate into the promoter region of the native LAC4 locus in the *K. lactis* chromosome after digestion with SacII or BstXI and introduction into yeast cells. Additionally, *K. lactis* DNA that directs integration of the vector into the *K. lactis* chromosome at locations other than LAC4 can be inserted into the vector. Any DNA containing a bacterial origin of replication and a selectable marker gene can be used in place of the pUC19 DNA sequence. The position of the wild-type $P_{LAC4}$ sequence, or any $P_{LAC4}$ mutant or hybrid cloned into pGBN1 is immediately upstream of the coding region for the secretion leader sequence.

Additionally, pGBN1 contains DNA encoding the Sc α-MF pre-pro domain immediately downstream of $P_{LAC4}$ to direct secretion of heterologously expressed proteins. Finally, pGBN1 carries a geneticin (G418) resistance gene expressed from the $P_{ADH1}$ for dominant selection in yeast. To create plasmid pGBN1$_{PGK1}$ a PmlI/HindIII fragment containing 488 base pairs of the *S. cerevisiae* PGK1 promoter was cloned into the HpaI/HindIII sites of plasmid pGBN1 to replace 1067 base pairs of native $P_{LAC4}$ (FIG. 2B). Primer P1 and primer P2 were used to amplify 283 base pairs of the *S. cerevisiae* PGK1 promoter using plasmid pGBN1$_{PGK1}$ as a template. The 283 bp fragment was cloned into the SnaBI/HindIII sites of plasmid pGBN1 to produce plasmid pGBN1$_{Hyb}$. Primer P3 was designed to incorporate mutations into the putative Pribnow box-like sequence (PBI) that lies upstream of the *E. coli* major transcription start site as detailed in FIG. 2B. Primers P2 and P3 were used to amplify a $P_{LAC4}$ fragment containing mutations in PBI using plasmid pGBN1 as a template. Amplified DNA from this initial PCR was used as template for a second PCR using primers P2 and P4. The final DNA product was cloned into the SnaBI/HindIII sites of plasmid pGBN1 to produce plasmid pGBN1$_{PB1}$. A PCR knitting method was used to mutate the PBII and PBIII sequences (FIG. 2B) that lie upstream of the *E. coli* minor transcription start site using complementary primers P5 and P6. Primers P2 and P5 and primers P4 and P6 were used to amplify 586 bp and 160 bp mutated $P_{LAC4}$ DNA fragments, respectively. Each amplified DNA product was purified by QiaQuick™ PCR purification spin column chromatography (Qiagen, Valencia, Calif.) and combined as template in a second amplification reaction containing primers P2 and P4. The amplified $P_{LAC4}$ DNA fragment containing mutagenized PBII and PBIII sites was cloned into the SnaBI/Hind III sites of plasmid pGBN1 to produce plasmid pGBN1$_{PBII-PBIII}$.

Targeted Mutagenesis of Pribnow Box-Like Sequences in $P_{LAC4}$

A series of four $P_{LAC4}$ variants were generated to eliminate the E. coli promoter activity of $P_{LAC4}$ by either replacing or introducing point mutations in PBI and PBII/PBIII as shown in FIG. 2B.

(i) Vector pGBN1$_{pGK1}$ incorporates 485 bp of the S. cerevisae PGK1 promoter ($P_{PGK1}$) in place of 1067 bp of native $P_{LAC4}$ thereby removing both galactose-responsive upstream activating sequences (UASI and UASII) and all three Pribnow box-like sequences.

(ii) Vector pGBN1$_{Hyb}$ incorporates 283 bp from the 3' end of P $P_{PGK1}$ in place of 283 bp comprising the 3' end of $P_{LAC4}$ resulting in deletion of all three Pribnow box-like sequences but leaving both UAS sequences intact.

(iii) Vector pGBN1$_{PB1}$ contains 6-point mutations that eliminate the Pribnow consensus sequence of PBI between nucleotides −204 and −209 of $P_{LAC4}$.

(iv) Vector pGBN1$_{PBII-PBIII}$ contains 5-point mutations that eliminate the Pribnow consensus sequences of PBII and PBIII between nucleotides −136 and −144 of $P_{LAC4}$.

Cloning and Expression Analysis of GFP in E. coli

GFP was PCR amplified with primers P7 and P8 using plasmid pGFPuv (Clontech, Palo Alto, Calif.) as a template. Amplified GFP was cloned in-frame with the α-MF pre-pro domain in the BglII/NotI sites of the various PGBN vectors (see previous section). Lysates of bacteria containing various pGBN-GFP constructs were prepared from 50 ml overnight cultures grown at 30° C. in LB medium containing 100 µg/ml ampicillin. Cultures were centrifuged and the cell pellets were frozen on dry ice, thawed at room temperature and resuspended in 10 µl of lysis buffer (20 mM Tris-HCl pH 7.5 containing 50 mM NaCl, 1 mM EDTA). The cells were disrupted with a Sonicator™ (Heat Systems-Ultrasonics, Plainview, N.Y.) for 15 s on setting 7, and cell debris was removed by centrifugation at 15,000×g for 10 minutes. The protein concentration of each lysate was determined by measuring its absorbance at 280 nm. Proteins (100 µg) in each lysate were separated on a Tris-glycine 10-20% SDS-polyacrylamide gel, transferred to nitrocellulose and blocked overnight in phosphate-buffered saline containing 0.05% Tween 20 (PBS-T) and 50% non-fat milk (w/v) at 4° C. An anti-GFP monoclonal antibody (Clontech, Palo Alto, Calif.) diluted 1:1000 in PBS-T containing 5% non-fat milk was used to probe the blot followed by incubation with a horseradish peroxidase-coupled anti-mouse secondary antibody (KPL, Gaithersberg, Md.) diluted 1:2000 in PBS-T containing 5% non-fat milk. Protein-antibody complexes were detected using LumiGlo detection reagents (Cell Signaling Technology, Beverly, Mass.). The amount of GFP produced in E. coli was measured by densitometry using a molecular imager FX (Bio-Rad, Hercules, Calif.) and Quantity One software.

Each $P_{LAC4}$ variant was tested for its ability to drive E. coli expression of a reporter gene encoding GFP that was cloned in-frame with the S. cerevisiae α-mating factor pre-pro domain in each of the pGBN vectors. The presence of GFP produced from $P_{LAC4}$ variants in E. coli lysates was analyzed by Western analysis. Removal of the PBI sequence by mutation resulted in an 87% decrease in GFP expression (FIG. 3A, lane 5), as determined by densitometry, relative to GFP produced by the wild-type $P_{LAC4}$ (FIG. 3A, lane 2). However, mutation of both PBII and PBIII sequences (FIG. 3A, lane 6) did not detectably down-regulate GFP expression. Deletion of all three Pribnow box-like sequences from $P_{LAC4}$ by replacement with $P_{PGK1}$ DNA (FIG. 3A, lanes 3 and 4) lead to a complete loss of detectable GFP expression. These results indicate that the majority of $P_{LAC4}$ expression in E. coli is dependent upon the presence of the PBI sequence.

Cloning and Expression of Enterokinase and HSA in K. lactis

Primers P9 and P10 were used to amplify the gene encoding HSA that was subsequently cloned in frame with the α-MF sequence in the XhoI/NotI sites of the various pGBN vectors. Primer P9 was designed to encode the K. lactis Kex1 protease cleavage site (KR↓) immediately upstream of the HSA open reading frame to ensure correct processing of the protein in the Golgi. K. lactis strains containing integrated pGBN-HSA DNA were grown in 2 ml cultures of YPGal for 48 hours at 30° C. The level of HSA secretion was visually assessed by separation of 15 µl of spent culture medium on 10-20% Tris-Glycine gels followed by Coomassie staining. A DNA fragment encoding the $EK_L$ was PCR amplified with primers P11 and P12 and cloned in-frame with the α-MF pre-pro domain in the XhoI/BglII restriction sites of the various pGBN vectors containing the PLAC4 variants or in the vector pKLAC1 (see below). The DNA sequence of $EK_L$ in the various pGBN-$EK_L$ or pKLAC1-$EK_L$ vectors was confirmed by nucleotide sequencing. Secretion of enterokinase by K. lactis strains containing integrated pKLAC1-$EK_L$ constructs was assessed by growing cells in 2 ml YPGal for 48 hours at 30° C. and assaying spent culture medium for enterokinase activity as described below.

Enterokinase Activity Assay

Spent culture medium was isolated by microcentrifugation of 1 ml of a saturated culture of pKLAC1-$EK_L$ integrated K. lactis at 15,800×g for 1 minute to remove cells. Enterokinase activity was measured using the fluorogenic peptide substrate GDDDDK-β-napthylamide (Bachem, King of Prussia, Pa.). Spent culture medium (50 µl) was mixed with 50 µl enterokinase assay buffer (124 mM Tris-HCl pH 8.0 containing 0.88 mM GD4K-β-napthylamide, 17.6% dimethylsulfoxide) and fluorescence intensity (excitation 337 nm, emission 420 nm) was measured over time. A comparison of the amount of enzyme activity associated with measured quantities of purified enterokinase (New England Biolabs, Beverly, Mass.) to the activity present in spent K. lactis culture medium was used to estimate the amount of active enterokinase secreted by K. lactis strains. To compensate for a mild inhibitory effect that YPGal culture medium has on the enterokinase assay, purified enterokinase was first diluted into spent medium from a culture of untransfected K. lactis cells prior to measuring enterokinase activity as described above.

$P_{LAC4}$ Variants Retain Full Promoter Activity in K. lactis

To test if the $P_{LAC4}$ variants were able to direct expression of a heterologous gene in K. lactis, the gene encoding HSA was cloned into each of the pGBN vectors. HSA was chosen as a reporter protein due to its high expression and efficient secretion from K. lactis when expressed from wild-type $P_{LAC4}$ (Fleer, et al. Bio. Technol. 9:968-975 (1991)). K. lactis strains containing each of the integrated pGBN1-HSA expression vectors were grown to saturation in YPGal medium and secreted proteins in the spent culture medium were separated by SDS-PAGE and detected by Coomassie staining. HSA migrates as a 66 kDa band that can readily be detected in unconcentrated spent culture medium, and its identity was confirmed by Western blotting with an anti-HSA antibody. $K.$ $lactis$ strains containing integrated pGBN1$_{PB1}$-HSA, pGBN1$_{Hyb}$-HSA and pGBN1$_{PBII\text{-}PBIII}$-HSA vectors secreted HSA in amounts comparable to a control strain harboring pGBN1-HSA where HSA is expressed from wild-type P$_{LAC4}$ (FIG. 3B, lane 2). These data indicate that mutation or deletion of the PBI, PBII and PBIII sequences of P$_{LAC4}$ does not significantly alter the promoter's ability to function in $K.$ $lactis$. It is also noteworthy that markedly less HSA was secreted from cells harboring pGBN1$_{PGK1}$-HSA (FIG. 3B, lane 3) compared to cells expressing HSA from either wild-type P$_{LAC4}$ (FIG. 3B, lane 2) or the other P$_{LAC4}$ variants (FIG. 3B, lanes 4-6). This is consistent with the notion that HSA expression from P$_{PGK1}$ is suppressed in galactose-containing medium because both UAS sequences required for galactose-induced expression have been deleted.

Effects of P$_{LAC4}$ Variants on the Cloning Efficiency of Bovine Enterokinase

Bovine enterokinase is a commercially important protease that is often used to cleave affinity tags from engineered fusion proteins. Commercial production of enterokinase in $E.$ $coli$ is plagued by low yields that are attributable to the protein's toxicity in bacteria.

Expression of enterokinase in $K.$ $lactis$ is shown here as a means to circumvent poor expression in bacteria. Numerous attempts to assemble $K.$ $lactis$ expression vectors in $E.$ $coli$, where DNA encoding the EK$_L$ was placed downstream of wild-type P$_{LAC4}$, resulted in widespread isolation of clones containing loss-of-function mutations (e.g. frame shifts or early terminations) within the EK$_L$-coding sequence. P$_{LAC4}$ variants that exhibited reduced or abolished expression in $E.$ $coli$ are shown here to facilitate cloning of the toxic EK$_L$ gene into $K.$ $lactis$ expression vectors in $E.$ $coli$ prior to their introduction into yeast. The EKL gene was PCR-amplified using a high-fidelity polymerase and cloned downstream of the various P$_{LAC4}$ variants in the pGBN1 vectors (see FIG. 2B). The entire EK$_L$ gene (708 bp) of numerous isolated clones was sequenced to determine the presence of loss-of-function mutations. When cloned under the control of wild-type P$_{LAC4}$ in pGBN1, 11 of 12 (92%) clones examined contained loss-of-function mutations. However, no mutations were found in EK$_L$ cloned in vectors pGBN1$_{PGK1}$ (9 clones sequenced) or pGBN1$_{Hyb}$ (7 clones sequenced), vectors containing P$_{LAC4}$ variants that completely lack $E.$ $coli$ promoter function. Additionally, no mutations were found in EK$_L$ cloned in vector PGBN1$_{PB1}$ (9 clones sequenced) where $E.$ $coli$ expression is reduced ~87% due to mutations in PBI. Additionally, 3 of 10 (30%) of EK$_L$ clones in pGBN1$_{PBII\text{-}PBIII}$ contained loss-of-function mutations. Together, these data show that the function of wild-type P$_{LAC4}$ in $E.$ $coli$ adversely affects the cloning efficiency of a toxic gene, and indicate that P$_{LAC4}$ variants that either lack or have severely reduced function in $E.$ $coli$ are better suited for the assembly of $K.$ $lactis$ expression constructs in bacteria.

Construction of pKLAC1, an Integrative $K.$ $lactis$ Expression Vector

A novel $K.$ $lactis$ integrative expression vector (pKLAC1) for commercial secretion of proteins from $K.$ $lactis$ has been created. This vector is based on the P$_{LAC4\text{-}PB1}$-variant that contains mutations in PBI (see FIG. 2B, pGBN1$_{PB1}$) and contains (in 5' to 3' order): a PBI-deficient LAC4 promoter, the $K.$ $lactis$ α-mating factor secretion leader sequence, a multiple cloning site, the $K.$ $lactis$ LAC4 transcription terminator, a selectable marker cassette containing the $Aspergillus$ $nidulans$ amdS gene expressed from the P$_{ADH1}$, and an $E.$ $coli$ origin of replication and ampicillin resistance gene to allow for its propagation in $E.$ $coli$.

Digestion of this vector with SacII or BstXI generates a linear expression cassette that integrates into the promoter region of the P$_{LAC4}$ locus of the $K.$ $lactis$ chromosome upon its introduction into $K.$ $lactis$ cells. Transformed yeast are isolated by nitrogen source selection on yeast carbon base medium containing 5 mM acetamide, which can be converted to a simple nitrogen source only if the expression cassette (containing the amdS gene) has integrated into the chromosome (U.S. Pat. No. 6,051,431).

DNA encoding the $K.$ $lactis$ α-MF pre-pro domain was PCR-amplified from $K.$ $lactis$ genomic DNA using primers 13 and 14 and cloned into the SacI/XhoI sites of pLitmus29 (New England Biolabs, Beverly, Mass.). The cloned $K.$ $lactis$ α-MF sequence was subsequently excised by HindIII1 and XhoI digestion and cloned into the HindIII/XhoI sites of plasmid pGBN1$_{PB1}$ to produce plasmid pGBN1$_{PB1}$-Kl α-MF. A 1520 bp DNA fragment containing all of the $A.$ $nidulans$ amdS gene except the first 128 bp was amplified using primers P15 and P16 and a cloned amdS gene as a template (DSM Biologics B.V., Delft, Netherlands). This fragment was cloned into the BamHI/SmaI sites of plasmid pGBN1$_{PB1}$-Kl α-MF replacing the G418 resistance gene and producing plasmid pGBN1$_{PB1}$-KL α-MF-1520. The remaining 128 bp of the 5' end of amdS gene was amplified by PCR with primers P16 and P17, digested with BamHI, cloned into the BamHI site of vector pGBN1$_{PB1}$-Kl α-MF-1520 and the proper orientation of the fragment was confirmed by DNA sequencing. The resulting vector is named pKLAC1 (GenBank Accession No. AY968582) and is commercially available from New England Biolabs, Beverly, Mass.

Vector pKLAC1 was used to secrete enterokinase from $K.$ $lactis$ cells after successfully assembling the expression vector in $E.$ $coli$ (pKLAC1-EK$_L$). Strains harboring integrated pKLAC1-EK$_L$ were cultured in YPGal medium for 2 days. Enterokinase proteolytic activity in the spent culture medium was assayed by measuring the rate of cleavage of a fluorogenic peptide. Measurements of activity performed on culture supernatant from seven pKLAC1-EK$_L$ integrated strains showed that all seven secreted active enterokinase (KLEK) (FIG. 5). However, two of the seven strains (KLEK-S1 and KLEK-S4) secreted greater levels of enterokinase activity than the other five. Southern analysis determined that strains KLEK-S1 and KLEK-S4 contained multiple tandem copies of integrated pKLAC1-EK$_L$. The yield of enterokinase secreted from strain KLEK-S1 grown in shake flasks was estimated to be ~1.1 mg/L based on a comparison of secreted enzyme activity to the activity of known quantities of purified enterokinase as described above.

TABLE 1

Oligonucleotides used in this study

| Primer | Sequence* |
|---|---|
| P1 | 5'-CTGTTACTCTCTCTCTTTCAAACAG-3' (SEQ ID NO:5) |
| P2 | 5'-GCATGTATACATCAGTATCTC-3' (SEQ ID NO:6) |
| P3 | 5'-GGTATTTAATAGCTCGAATCAATGTGAGAACAGAGAGAAGATGTTCTTCCCTAACTC-3' (SEQ ID NO:7) |
| P4 | 5'-GTAATGTTTTCATTGCTGTTTTACTTGAGATTTCGATTGAGAAAAAGGTATTTAATAGCTC |
| P5 | GAATCAATG-3' (SEQ ID NO:8) |
| P6 | 5'-GTTTCTTAGGAGAATGAGAGCTCTTTTGTTATGTTGC-3' (SEQ ID NO:9) |
| P7 | 5'-GCAACATAACAAAAGAGCTCTCATTCTCCTAAGAAAC-3' (SEQ ID NO:10) |
| P8 | 5'-GGAAGATCTATGAGTAAAGGAGAAGAACTT-3' (SEQ ID NO:11) |
| P9 | 5'-ATAAGAATGCGGCCGCTTATTTGTAGAGCTCATCCATGCC-3' (SEQ ID NO:12) |
| P10 | 5'-CCGCTCGAGAAAAGAGATGCACACAAGAGTGAGGTTGCT-3' (SEQ ID NO:13) |
| P11 | 5'-ATAAGAATGCGGCCGCTTATAAGCCTAAGGCAGC-3' (SEQ ID NO:14) |
| P12 | 5'-CCGCTCGAGAAAAGAATTGTTGGTGGTTCTGATTCTAGA-3' (SEQ ID NO:15) |
| P13 | 5'-GGAAGATCTCTAATGTAGAAAACTTTGTATCC-3' (SEQ ID NO:16) |
| P14 | 5'-TCCGAGCTCAAGCTTGAAAAAAATGAAATTCTCTACTATATTAGCC-3' (SEQ ID NO:17) |
| P15 | 5'-CCGCTCGAGATCATCCTTGTCAGCGAAAGC-3' (SEQ ID NO:18) <br> 5'-CGGGGATCCTTTCAGAGGCCGAACTGAAGATCACAGAGGCTTCCGCTGCGGATCTTGTG |
| P16 | TCCAAGCTGGCGGCCGGA-3' (SEQ ID NO:19) |
| P17 | 5'-TCCCCCGGGCTATGGAGTCACCACATTTCCCAGCAA-3' (SEQ ID NO:20) <br> 5'-CGCGGATCCGCCACCATGCCTCAATCCTGGGAAGAA-3' (SEQ ID NO:21) |

*Engineered restriction sites are underlined.

What is claimed is:

1. A method of producing a recombinant protein in yeast cells, comprising:
   (a) obtaining a vector into which a gene encoding the target protein has been inserted, the vector further comprising: a modified $P_{LAC4}$ having a mutation in one or more Pribnow box-like sequences wherein the modification results in a significant reduction in gene expression when the vector is cloned in bacteria;
   (b) transforming yeast cells with the vector; and
   (c) producing an effective amount of the recombinant protein in the yeast cells.

2. A method according to claim 1, wherein the one or more Pribnow box-like sequences are PBI, PBII and PBIII.

3. A method according to claim 1, wherein the mutation is in two or more Pribnow box-like sequences.

4. A method according to claim 1, wherein the modified $P_{LAC4}$ has one or more mutations in a first region of the promoter corresponding to nucleotides −198 to −212.

5. A method according to claim 1, wherein the modified $P_{LAC4}$ has one or more mutations in a second region of the promoter corresponding to nucleotides −133 to −146.

6. A method according to claim 1, wherein nucleotides −1 to −283 in the modified $P_{LAC4}$ are substituted by nucleotides −1 to −283 of a phosphoglycerate kinase promoter from S. cerevisiae.

7. A method according to claim 1, wherein the vector in the transformed yeast cells is an episomal plasmid.

8. A method according to claim 1, wherein the vector in the transformed yeast cells is an integrative plasmid.

9. A vector, comprising: a modified $P_{LAC4}$ promoter having a mutation in one or more Pribnow box-like sequences operatively linked to a gene encoding a target protein.

10. A vector according to claim 9, wherein the one or more Pribnow box-like sequences are PBI, PBII and PBIII.

11. A vector according to claim 9, wherein the mutation is in two or more Pribnow box-like sequences.

12. A vector according to claim 9, wherein the modified $P_{LAC4}$ has one or more mutations in a first region of the promoter corresponding to nucleotides −198 to −212.

13. A vector according to claim 9, wherein the modified $P_{LAC4}$ has one or more mutations in a second region of the promoter corresponding to nucleotides −133 to −146.

14. A vector according to claim 9, wherein nucleotides −1 to −283 in the modified $P_{LAC4}$ are substituted by nucleotides −1 to −283 of a phosphoglycerate kinase promoter from S. cerevisiae.

15. A host yeast cell comprising a vector of claim 9.

16. A kit, comprising: a vector according to claim 9; and optionally, competent yeast cells and instructions for use.

* * * * *